US009375230B2

(12) United States Patent
Ross et al.

(10) Patent No.: US 9,375,230 B2
(45) Date of Patent: Jun. 28, 2016

(54) ULTRASONIC SURGICAL INSTRUMENTS

(75) Inventors: Anthony B. Ross, Boulder, CO (US);
Robert B. Stoddard, Steamboat Springs, CO (US); James S. Cunningham, Boulder, CO (US); William J. Dickhans, Longmont, CO (US); Russell D. Hempstead, Lafayette, CO (US); Eric R. Larson, Boulder, CO (US); Duane E. Kerr, Jr., Loveland, CO (US); William H. Nau, Jr., Longmont, CO (US); Arlen K. Ward, Thornton, CO (US)

(73) Assignee: COVIDIEN LP, Mansfiled, MA (US)

( * ) Notice: Subject to any disclaimer, the term of this patent is extended or adjusted under 35 U.S.C. 154(b) by 285 days.

(21) Appl. No.: 14/006,532

(22) PCT Filed: Mar. 30, 2012

(86) PCT No.: PCT/US2012/031612
§ 371 (c)(1),
(2), (4) Date: Sep. 20, 2013

(87) PCT Pub. No.: WO2012/135721
PCT Pub. Date: Oct. 4, 2012

(65) Prior Publication Data
US 2014/0012297 A1 Jan. 9, 2014

Related U.S. Application Data

(60) Provisional application No. 61/469,565, filed on Mar. 30, 2011, provisional application No. 61/469,593, filed on Mar. 30, 2011.

(51) Int. Cl.
*A61B 17/32* (2006.01)
*A61B 17/00* (2006.01)
*A61B 18/00* (2006.01)

(52) U.S. Cl.
CPC ......... *A61B 17/320092* (2013.01); *A61B 90/04* (2016.02); *A61B 2017/00088* (2013.01);
(Continued)

(58) Field of Classification Search
CPC ............... A61B 19/40; A61B 2017/00088; A61B 2017/00092; A61B 2018/00095; A61B 2018/00101; A61B 2018/00595; A61B 2018/00601; A61B 2018/00083; A61B 2019/4072; A61N 7/00; A61N 2007/0004; A61N 2007/0008
USPC .................................................... 606/169
See application file for complete search history.

(56) References Cited

U.S. PATENT DOCUMENTS 3,076,904 A 2/1963 Kleesattel et al.
6,454,781 B1 9/2002 Witt et al.
(Continued)

FOREIGN PATENT DOCUMENTS

DE 3507672 A1 9/1986
DE 3630478 C1 1/1988
(Continued)

OTHER PUBLICATIONS

Supplementary Partial European Search Report from corresponding EP 12764956 dated Mar. 18, 2015.

*Primary Examiner* — Jonathan W Miles
*Assistant Examiner* — Majid Jamialahmadi

(57) ABSTRACT

An ultrasonic surgical instrument is provided. The ultrasonic surgical instrument includes a housing having an elongated shaft extending therefrom. The shaft defines a longitudinal axis therethrough and has at least one jaw member disposed at a distal end thereof. The jaw member(s) is movable between open and clamping configurations. A probe extends through the shaft and operably couples to the housing. The probe includes a cutting blade at a distal end thereof adjacent the jaw member(s) to treat tissue of interest. The jaw member(s) and cutting blade are configured such that heat damage to tissue adjacent tissue of interest that has been treated by the cutting blade is reduced and/or eliminated.

6 Claims, 3 Drawing Sheets

(52) U.S. Cl.
CPC .......... *A61B2017/00092* (2013.01); *A61B 2017/00336* (2013.01); *A61B 2018/00095* (2013.01); *A61B 2018/00101* (2013.01); *A61B 2090/0472* (2016.02)

(56) References Cited

U.S. PATENT DOCUMENTS

| | | | |
|---|---|---|---|
| 6,669,690 B1 | 12/2003 | Okada et al. | |
| 7,108,695 B2 | 9/2006 | Witt et al. | |
| 8,258,886 B2 | 9/2012 | Gilbert | |
| 8,373,572 B2 | 2/2013 | Dycus | |
| 8,662,745 B2 | 3/2014 | Misuchenko et al. | |
| 8,665,031 B2 | 3/2014 | Gilbert | |
| 2002/0183774 A1 | 12/2002 | Witt et al. | |
| 2006/0217706 A1* | 9/2006 | Lau | A61B 17/29 606/45 |
| 2006/0259054 A1 | 11/2006 | Masuda et al. | |
| 2007/0043352 A1* | 2/2007 | Garrison | A61B 18/1445 606/51 |
| 2008/0234708 A1 | 9/2008 | Houser et al. | |
| 2009/0030311 A1 | 1/2009 | Stulen et al. | |
| 2009/0030437 A1 | 1/2009 | Houser et al. | |
| 2009/0036913 A1 | 2/2009 | Wiener et al. | |
| 2009/0036914 A1* | 2/2009 | Houser | A61B 17/320068 606/169 |
| 2009/0048589 A1* | 2/2009 | Takashino | A61B 17/07207 606/28 |
| 2009/0143795 A1* | 6/2009 | Robertson | A61B 17/320092 606/169 |
| 2010/0312252 A1* | 12/2010 | Jia | A61B 18/10 606/107 |
| 2013/0127625 A1 | 5/2013 | Dycus | |
| 2013/0197511 A1 | 8/2013 | Balanev et al. | |
| 2013/0231664 A1 | 9/2013 | Balanev et al. | |
| 2013/0325047 A1 | 12/2013 | Craig | |
| 2013/0331873 A1 | 12/2013 | Ross et al. | |
| 2013/0331874 A1 | 12/2013 | Ross et al. | |
| 2013/0331875 A1 | 12/2013 | Ross et al. | |
| 2014/0012297 A1 | 1/2014 | Ross et al. | |
| 2014/0012298 A1 | 1/2014 | Cunningham et al. | |
| 2014/0012299 A1 | 1/2014 | Stoddard et al. | |
| 2014/0017118 A1 | 1/2014 | Stoddard et al. | |

FOREIGN PATENT DOCUMENTS

| | | |
|---|---|---|
| DE | 10141385 A1 | 7/2002 |
| DE | 20118698 U1 | 4/2003 |
| DE | 20118699 U1 | 4/2003 |
| DE | 20303776 U1 | 7/2004 |
| JP | 61096419 A | 5/1986 |
| JP | 02034008 A | 2/1990 |
| JP | 06114069 A | 4/1994 |
| JP | 2001212514 A | 8/2001 |
| JP | 2001346805 A | 12/2001 |
| JP | 2002045368 A | 2/2002 |
| JP | 2002186901 A | 2/2002 |
| JP | 2002-237204 | 8/2002 |
| JP | 2004254128 A | 9/2004 |
| JP | 3696034 B2 | 7/2005 |
| JP | 3756726 B2 | 1/2006 |
| WO | 2005/076968 A2 | 8/2005 |
| WO | WO 2005/122917 A1 | 12/2005 |
| WO | WO 2006/101644 A2 | 9/2006 |
| WO | WO 2007/014548 A2 | 2/2007 |
| WO | WO 2008/012357 A1 | 1/2008 |
| WO | WO 2008/012359 A1 | 1/2008 |
| WO | WO 2008/051764 A2 | 5/2008 |
| WO | WO 2008/065323 A1 | 6/2008 |
| WO | WO 2008/118709 A1 | 10/2008 |

\* cited by examiner

ULTRASONIC SURGICAL INSTRUMENTS

CROSS-REFERENCE TO RELATED APPLICATIONS

The present application claims the benefit of and priority to U.S. Provisional Application No. 61/469,593 filed on Mar. 30, 2011 by Ross et al. and U.S. Provisional Application No. 61/469,565 filed on Mar. 30, 2011 by Ross et al., the entire contents of both of which are incorporated herein by reference.

BACKGROUND

1. Technical Field

The present disclosure relates to ultrasonic surgical instruments. More particularly, the present disclosure relates to ultrasonic surgical instruments configured to minimize heat damage to tissue adjacent the tissue of interest.

2. Description of Related Art

Ultrasonic energy-powered instruments configured to cut and/or fragment tissue are known in the art. Ultrasonic instruments, typically, include a transducer that is coupled to a probe/waveguide having an active member (e.g., cutting blade, shear, hook, ball, etc.) at a distal end thereof. In use, ultrasonic energy is utilized to vibrate (e.g., at frequency usually in the range of 20 KHz to 60 KHz) the active member to treat tissue of interest.

Ultrasonic instruments may include any of a variety of probe configurations to achieve a specific surgical result. For example, the probe configuration may include an active member in the form of a cutting blade that is combined with a movable jaw configured to grasp and/or manipulate tissue. Such ultrasonic instruments are primarily used in a variety of medical procedures including open surgical procedures, luminal procedures, and endoscopic procedures.

During use, the active member, e.g., the cutting blade, may reach temperatures greater than 200° C. At such temperatures, inadvertent contact between the cutting blade, such as, for example, a lower portion thereof, and tissue, e.g., tissue adjacent the tissue of interest, may cause undesirable heat damage to the tissue.

SUMMARY

In view of the foregoing, ultrasonic instruments configured to minimize heat damage to tissue adjacent tissue of interest that has been ultrasonically treated may prove useful in the medical art.

Embodiments of the present disclosure are described in detail with reference to the drawing figures wherein like reference numerals identify similar or identical elements. As used herein, the term "distal" refers to a portion that is being described which is further from a user, while the term "proximal" refers to a portion that is being described which is closer to a user.

An aspect of the present disclosure provides an ultrasonic surgical instrument. The ultrasonic instrument includes a housing having an elongated shaft extending therefrom. The shaft defines a longitudinal axis therethrough and has a pair of first and second jaw members disposed at a distal end thereof. The first jaw member is movable between an open configuration and a clamping configuration and the second jaw member is translatable along the longitudinal axis from a retracted configuration to an extended configuration. A lever may be operably coupled to the housing and configured to move the first jaw member between the open and clamping configurations. A cutting blade extends at the distal end of the shaft and operably couples to the housing and adjacent the first and second jaw members. The cutting element is coupled to a probe that extends within the shaft. The second jaw member is moveable to the extended configuration to cover a bottom portion of the cutting blade to reduce heat damage to tissue adjacent tissue of interest that has been treated by the cutting blade.

A switching mechanism may be disposed on the ultrasonic surgical instrument and configured to actuate the second jaw member to move the second jaw member from the retracted configuration to the extended configuration.

At least a portion of the second jaw member may be made from a material having high thermal conductivity to facilitate cooling of the cutting blade. Moreover, a bottom portion of the second jaw member may be covered with an insulative material to reduce thermal spread from the second jaw member to tissue adjacent the tissue of interest. The second jaw member may include at least one temperature sensor thereon configured to detect a temperature of the cutting blade. The temperature sensor(s) may be, but is not limited to, thermocouple or a thermistor.

An aspect of the present disclosure provides an ultrasonic surgical instrument. The ultrasonic surgical instrument includes a housing having an elongated shaft extending therefrom. The shaft defines a longitudinal axis therethrough and has a jaw member disposed at a distal end thereof. The jaw member is movable between an open configuration and a clamping configuration. A sheath operably couples to the housing and is coaxially disposed along shaft. The sheath is translatable along the longitudinal axis from a retracted configuration to an extended configuration. A cutting blade extends at a distal end of the shaft and operably couples to the housing and adjacent the jaw member. The sheath is moveable to the extended configuration to cover at least the cutting blade to reduce heat damage to tissue adjacent tissue of interest that has been treated by the cutting blade.

A switching mechanism may be disposed on the ultrasonic surgical instrument and configured to actuate the sheath to move the sheath from the retracted configuration to the extended configuration.

At least a portion of an interior surface of the sheath may be made from a material having a high thermal conductivity to facilitate cooling the cutting blade. An exterior surface of the sheath may be covered with an insulative material to reduce thermal spread from the sheath to tissue adjacent tissue of interest.

The sheath may include at least one temperature sensor thereon configured to detect a temperature of the cutting blade. The temperature sensor(s) may be, but is not limited to, thermocouple or a thermistor.

An aspect of the present disclosure provides an ultrasonic surgical instrument. The ultrasonic surgical instrument includes a housing having an elongated shaft extending therefrom. The shaft defines a longitudinal axis therethrough and has a first jaw member disposed at a distal end thereof. The first jaw member is movable between open and clamping configurations. A cutting blade extends at a distal end of the shaft and operably couples to the housing and adjacent the first jaw member. The cutting blade is translatable along the longitudinal axis from a retracted configuration within the shaft to an extended configuration outside the shaft to treat tissue of interest. The cutting blade is moveable to the retracted configuration within the shaft to reduce heat damage to tissue adjacent tissue of interest that has been treated by the cutting blade.

A switching mechanism may be disposed on the housing and configured to actuate the cutting blade to move the cutting blade from the retracted configuration to the extended configuration.

The shaft may include at least one temperature sensor thereon configured to detect a temperature thereof. The temperature sensor(s) may be, but is not limited to, thermocouple or a thermistor.

The ultrasonic surgical instrument may further include a second jaw member that is pivotably coupled to the first jaw member and configured to move between an open configuration and a clamping configuration to facilitate clamping tissue.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
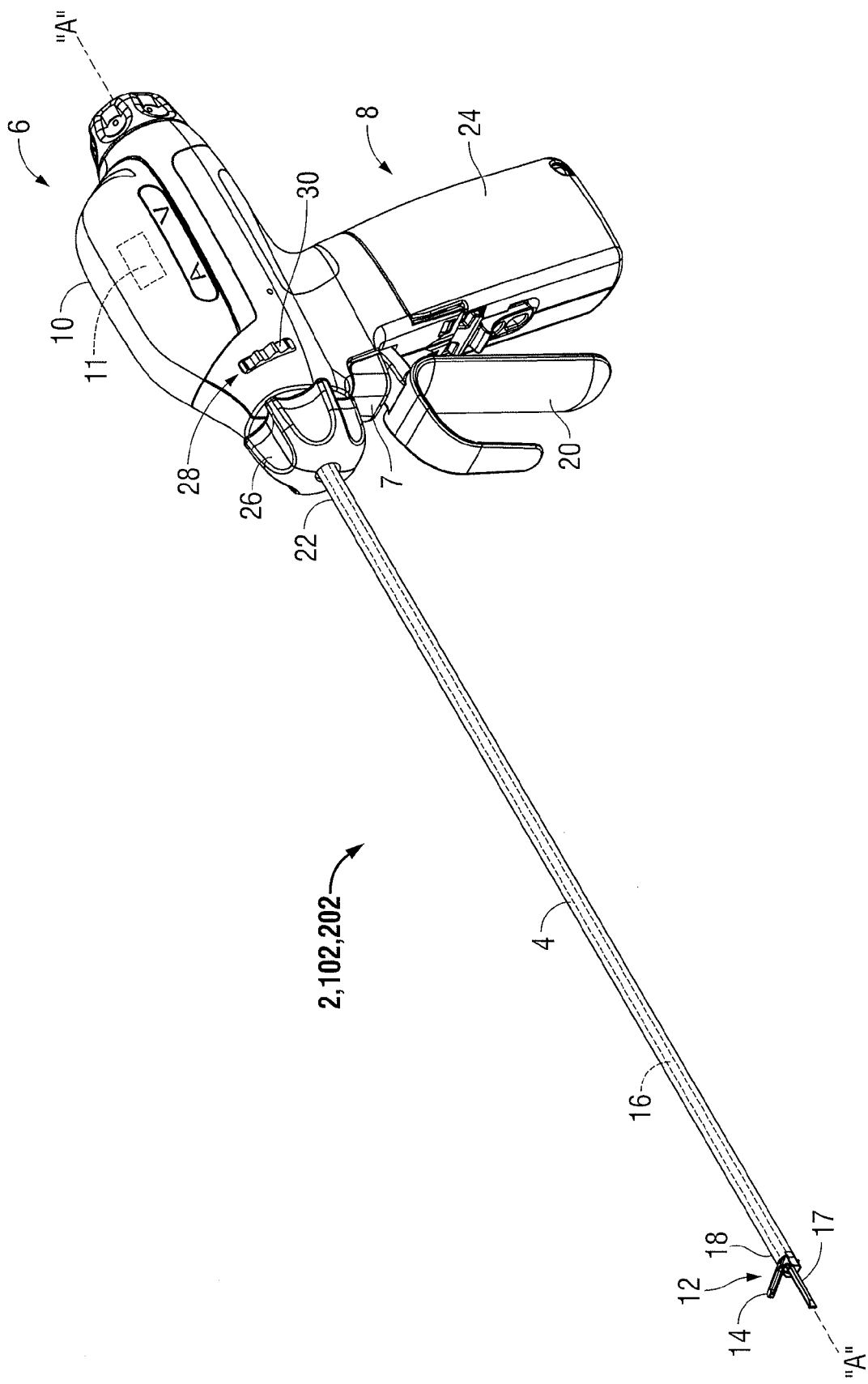
FIG. 1 is a right, perspective view of an ultrasonic instrument according to an embodiment of the present disclosure.

Turning now to FIG. 1, an ultrasonic surgical instrument 2 (instrument 2) according to an embodiment of the present disclosure is illustrated. In the illustrated embodiments, the instrument 2 is described herein as being battery powered. Alternatively, the instrument 2 may be externally powered, e.g., via a remote ultrasonic generator that is coupleable to the instrument 2.

Briefly, instrument 2 includes a housing 6 configured to house one or more components, e.g., transducer (not explicitly shown), a probe 16, and electrical circuitry that is configured for electrical communication with a battery assembly 8 of the instrument 2. A proximal end of housing 6 is configured to releasably couple to an ultrasonic generator 10 and the battery assembly 8. A distal end of the housing 6 is configured to support and/or couple to a proximal end 22 of a shaft 4 having a longitudinal axis "A-A" defined therethrough. A rotation knob 26 operably couples to housing 6 and is configured to rotate the shaft 4 approximately 360° in either direction about the longitudinal axis "A-A." Generator 10 includes the transducer that is coupled to the probe 16 via a torque adapter (not explicitly shown) and configured to produce vibratory motion of a cutting blade 17 disposed at a distal end of the probe 16 when a trigger 7 is depressed. This vibratory motion of the cutting blade 17 is utilized to treat tissue of interest. Battery assembly 8 includes a handpiece 24 having a battery (not explicitly shown) operably disposed therein.

Figure 2:
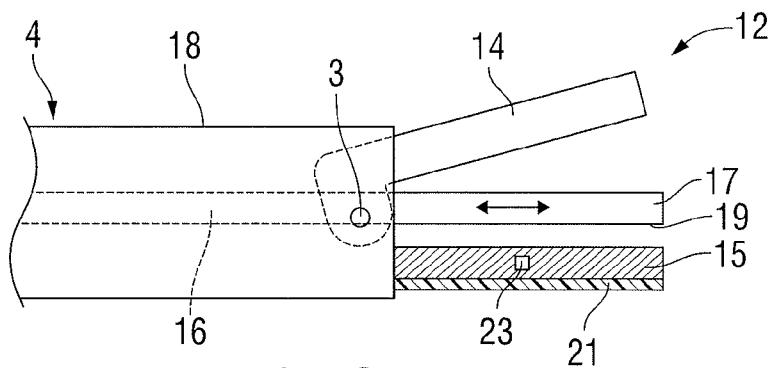
FIG. 2 is an enlarged, side, schematic view of a distal end of the ultrasonic instrument depicted in FIG. 1 with a bottom jaw member illustrated in an extended configuration.
Figure 3:
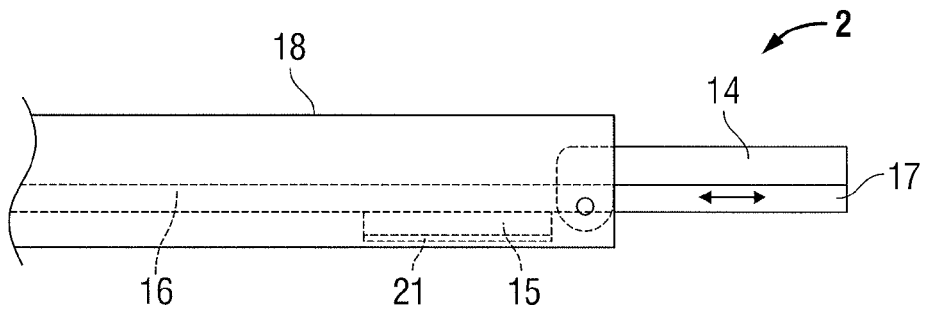
FIG. 3 is an enlarged, side, schematic of the distal end depicted in FIG. 2 with the bottom jaw member illustrated in a retracted configuration.

With reference to FIGS. 2-3, an end effector 12 includes a pair of first and second jaw members 14 and 15 that are supported at a distal end 18 of the shaft 4 adjacent cutting blade 17.

Jaw member 14 is pivotably supported at the distal end of the shaft 4 via a pivot pin 3 (FIG. 2) and functions as a "clamping jaw." In particular, jaw member 14 is movable relative to the cutting blade 17 (and/or the distal end 18 of the shaft 4) between an open configuration (FIGS. 1 and 2) and a clamping configuration (FIG. 3) to clamp tissue when a lever or movable handle 20 (FIG. 1) is actuated. Jaw member 14 and cutting blade 17 are configured to collectively grasp and ultrasonically treat tissue. In particular, with tissue positioned between the jaw member 14 and cutting blade 17, the cutting blade is configured to vibrate at a specific frequency (e.g., at a frequency in the range from about 20 KHz to about 60 KHz) to treat tissue.

Continuing with reference to FIGS. 2 and 3, jaw member 15 is translatable along the longitudinal axis "A-A" from a retracted configuration (FIGS. 1 and 3) to an extended configuration (FIG. 2). In the extended configuration, jaw member 15 is configured to cover (or shield) a bottom portion 19 of the cutting blade 17 to prevent or reduce inadvertent contact between the heated cutting blade 17 and tissue, e.g., tissue that is adjacent tissue of interest that has been ultrasonically treated or is being ultrasonically treated by the cutting blade 17.

Jaw member 15 may be configured to function as a heat sink and dissipate heat from the cutting blade 17 into one or more suitable mediums, e.g., air, to facilitate cooling of cutting blade 17. To this end, jaw member 15 may be made from any suitable material including, but not limited to metal, plastic, ceramic, etc. In the embodiment illustrated in FIGS. 1-3, jaw member 15 is made from a material, e.g., metal (suitable metals may include aluminum alloys, copper, tungsten, etc.), having high thermal conductivity (or high thermal mass) to facilitate cooling cutting blade 17 when the jaw member 15 is positioned adjacent thereto.

In embodiments, it may prove advantageous to provide a portion of the jaw member with diamond (or diamond dust), which has high thermal conductivity, to facilitate cooling the cutting blade 17. Additionally, or alternatively, in some embodiments, it may prove advantageous to mix diamond or synthetic diamond with one or more of the aforementioned metals. In some embodiments, it may prove advantageous to form the jaw member 15 entirely out of diamond or synthetic diamond material.

In embodiments, a bottom portion 21 of the jaw member 15 may be covered with an insulative material, e.g., plastic, ceramic, etc., to reduce thermal spread from the jaw member 15 to tissue adjacent the tissue of interest and/or the shaft 4. In the illustrated embodiment, bottom portion 21 is formed from ceramic material.

One or more temperature sensors 23 (FIG. 2) may be positioned on jaw members 14 and 15. In the embodiment illustrated in FIGS. 1-3, for example, a temperature sensor 23 is positioned on the jaw member 15 and is configured to detect a temperature of the cutting blade 17 when the jaw member 15 is in the extended configuration, see, e.g., FIG. 2. With this purpose in mind, temperature sensor 23 may be any suitable type of temperature sensor including, but not limited to thermocouples, thermistors and the like.

Temperature sensor 23 may be configured to communicate with one or more modules of the generator 10 and/or the battery assembly 8. In one particular embodiment, for example, temperature sensor 23 may be configured to provide data pertaining to a temperature of the cutting blade 17 to a temperature control module 11 (FIG. 1) of the generator 10 and/or battery assembly 8. In the illustrated embodiments, temperature control module 11 is provided with the generator 10 (FIG. 1). The temperature control module 11 may analyze the data pertaining to temperature of the cutting blade 17 and utilize one or more control algorithms to control an output response of the transducer based on this data to regulate a vibration frequency of the probe 16 such that a desired temperature may be maintained at the cutting blade 17. In one particular embodiment, instrument 2 and the temperature control module 11 may be configured to provide one or more indications, e.g., an audio indication "A", a visual indication "V", and so forth, to a user indicating that the cutting blade 17 is sufficiently cooled or at a predetermined safe temperature (FIG. 1). As defined herein, a safe temperature of the cutting blade 17 is a temperature incapable of damaging tissue.

Referring again to FIG. 1, a switching mechanism 28 is disposed on the housing 6 and operably couples to jaw member 15 to actuate jaw member 15 and move jaw member 15 from the retracted configuration to the extended configuration. Switching mechanism 28 may be any suitable type of switching mechanism including but not limited to push-buttons, dials, slides, and the like. In accordance with the instant disclosure, switching mechanism 28 includes a dial 30 positioned at a distal end of the housing 6. Dial 30 is configured to move jaw member 15 to the extended configuration when the dial 30 is moved in a counter-clockwise direction and is configured to move jaw member 15 back to the retracted configuration when the dial 30 is moved in a clockwise direction. One or more components, such as, for example, drive rods, servos, links, gears and the like may be provided with the instrument 2 to provide mechanical and/or electrical communication between the dial 30 and jaw member 15.

During use of one particular embodiment of the instrument 2, tissue may be positioned between the jaw member 14 and the cutting blade 17. Subsequently, trigger 7 may be depressed to activate the cutting blade 17 to treat tissue of interest.

As noted above, the cutting blade 17 may become hot due to the vibratory motion thereof. In accordance with the instant disclosure, dial 30 may be actuated to move the jaw member 15 to the extended configuration (FIG. 2) to cover (or shield) cutting blade 17. As noted above, in the extended configuration, jaw member 15 may serve as a heat-sink as a result of the high thermal conductivity associated therewith to facilitate dissipating heat from cutting blade 17 for cooling thereof.

Once cutting blade 17 is sufficiently cooled, dial 30 may be actuated to move jaw member 15 back to the retracted configuration (FIGS. 1 and 3). In one particular embodiment, the sensor(s) 23 and temperature control module 11 may be utilized to monitor the temperature of cutting blade 17 and indicate (e.g., audio indication "A" or visual indication "V") to a user when cutting blade 17 is sufficiently cooled. In certain instances, in this cooled state, a user may employ the cutting blade 17 to grasp and/or manipulate tissue.

The unique configuration of the instrument 2 including the jaw member 15 overcomes the aforementioned drawbacks that are typically associated with conventional ultrasonic instruments. That is, the likelihood of heat damage occurring to tissue adjacent tissue of interest that has been ultrasonically treated by the cutting blade 17 is reduced, if not eliminated by the jaw member 15.

While the instrument 2 has been described herein as including a jaw member 15 that is configured to cover the cutting blade 17, other devices or methods may be utilized to cover the cutting blade 17 to prevent inadvertent contact between the hot cutting blade 17 and tissue.

Figure 4:
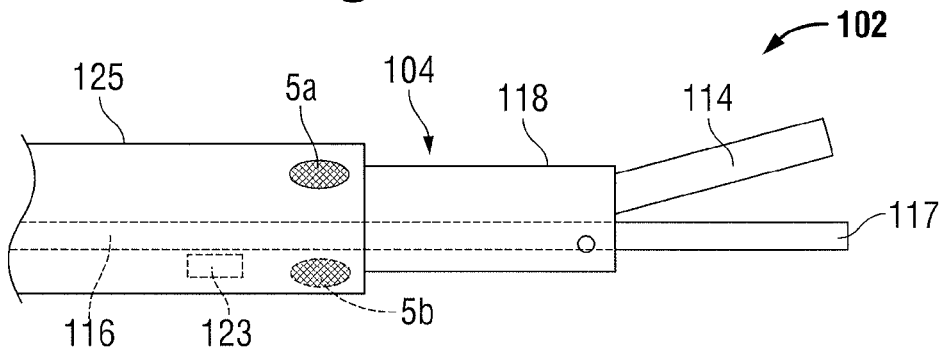
FIG. 4 is an enlarged, side, schematic of a distal end of an ultrasonic instrument according to another embodiment of the present disclosure with a protective sheath illustrated in a retracted configuration.
Figure 5:
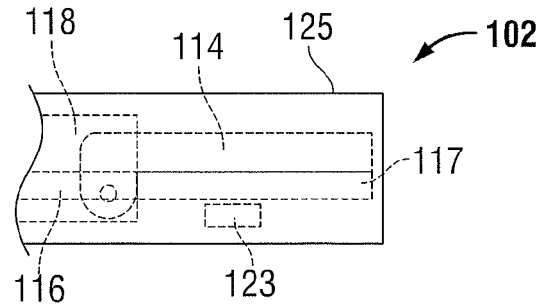
FIG. 5 is an enlarged, side, schematic with the protective sheath illustrated in an extended configuration.

With reference to FIGS. 4 and 5, the instrument 102 (FIG. 1) includes a sheath 125 that is configured to cover the cutting blade 117 and jaw member 114. Instrument 102 functions similarly to instrument 2, in view thereof only those features unique to instrument 102 are described in detail.

Sheath 125 operably couples to the housing 6 via one or more suitable coupling methods and is coaxially disposed along shaft 104. The sheath 125 is translatable along the longitudinal axis "A-A" from a retracted configuration (FIG. 4) to an extended configuration to cover at least a portion of the cutting blade 117 (and/or jaw member 114) to reduce heat damage to tissue adjacent tissue of interest that has been treated by cutting blade 117. In the embodiment illustrated in FIGS. 4 and 5, sheath 125 is configured to fully cover jaw member 114 and cutting blade 117.

Similar to jaw member 15, a portion of an interior surface of the sheath 125 is formed from a material 5*b* having high thermal conductivity to facilitate cooling the cutting blade 117. Additionally, or alternatively, an exterior surface of the sheath 125 is covered with an insulative material 5*a* to reduce thermal spread from sheath 125 to tissue adjacent tissue of interest. Further, one or more of the aforementioned temperature sensors 123 (FIGS. 4 and 5) may be disposed on sheath 125 and configured to detect a temperature of the cutting blade 117. In the embodiment illustrated in FIGS. 4 and 5, temperature sensor 123 is positioned on an interior surface of sheath 125 and is configured to function as described above with respect to sensor 23.

Unlike dial 30 that is operably coupled to the jaw member 15, dial 130 is coupled to the sheath 125 to actuate the sheath 125 and move the sheath 125 from the retracted configuration (FIG. 4) to the extended configuration (FIG. 5).

Operation of the instrument 102 that includes the sheath 125 is similar to that of instrument 2 that includes the jaw member 15. In particular, dial 130 may be actuated to move sheath 125 to the extended configuration (FIG. 5) to cover the cutting blade 117 and the jaw member 114. In the extended configuration, the sheath 125 serves as a "heat-sink" as a result of the high thermal conductivity thereof to facilitate cooling cutting blade 117.

The instrument 102 including the sheath 125 overcomes the aforementioned drawbacks typically associated with conventional ultrasonic surgical instruments and affords the same advantages as the instrument 2 to a user.

Figure 6:
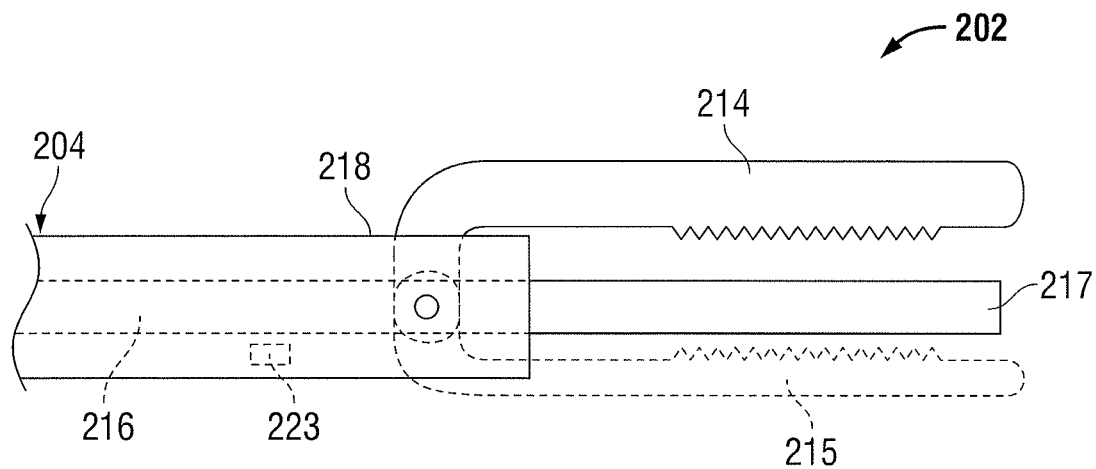
FIG. 6 is an enlarged, side, schematic of a distal end of an ultrasonic instrument according to yet another embodiment of the present disclosure with an cutting blade illustrated in an extended configuration.
Figure 7:
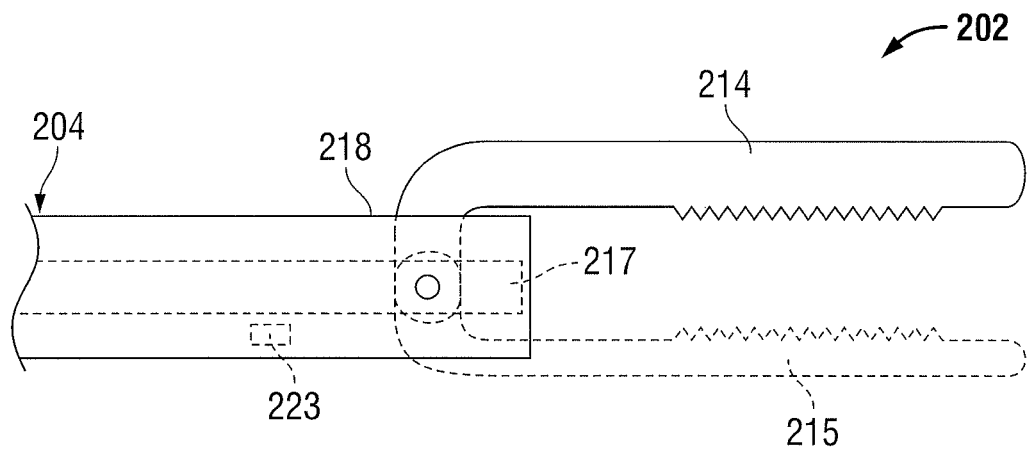
FIG. 7 is an enlarged, side, schematic with the cutting blade illustrated in a retracted configuration.

With reference to FIGS. 6 and 7, the instrument 202 (FIG. 1) includes a cutting blade 217. Instrument 202 functions similarly to instrument 2, therefore only those features unique to instrument 202 are described in detail.

Unlike the previously described cutting blades 17, 117, a cutting blade 217 is translatable along the longitudinal axis "A-A" from a retracted configuration (FIG. 7) within the shaft 218 to an extended configuration (FIG. 6) outside the shaft 218. In the extended configuration, cutting blade 217 and jaw member 214 are configured to treat tissue of interest as described hereinabove. As can be appreciated, heat damage to tissue adjacent the tissue of interest that has been treated by cutting blade 217 is reduced when cutting blade 217 in the retracted configuration.

One or more of the aforementioned temperature sensors 223 (FIGS. 6 and 7) may be disposed on an interior surface of the shaft 204 (FIGS. 6 and 7) and configured to function as described above with respect to sensors 23 and 123.

Unlike dials 30, 130 that operably couple to the jaw member 15 and sheath 125, respectively, dial 230 is coupled to the cutting blade 217 to actuate the cutting blade 217 and move the cutting blade 217 from the retracted configuration (FIG. 7) to the extended configuration (FIG. 6).

The instrument 202 including the cutting blade 217 overcomes the aforementioned drawbacks typically associated with conventional ultrasonic surgical instruments and affords the same advantages as the instruments 2, 102 to a user.

From the foregoing and with reference to the various figure drawings, those skilled in the art will appreciate that certain modifications can also be made to the present disclosure without departing from the scope of the same. For example, and in the embodiment illustrated in FIGS. 6 and 7, an optional second jaw member 215 (FIGS. 6 and 7 illustrate the optional second jaw member 215 in phantom) may be provided with the instrument 202 to facilitate grasping and/or manipulating tissue, such as, for example, when the cutting blade 217 is in the retracted configuration, see FIG. 7. In this particular embodiment, the movable handle 20 may be configured to move jaw member 215 from an open configuration to a clamping configuration. For example, the movable handle 20 may be configured to move through a first clamping stroke to close the jaw member 214 and through a second clamping stroke to close the jaw member 215. Those skilled in the art will appreciate other methods of opening and closing jaw member 215.

In embodiments, the aforementioned jaw members 14, 15, 114, 214 and 215 may be provided with a relatively flat tissue contacting surface (FIGS. 1-5) or a serrated tissue contacting surface (FIGS. 6 and 7). The specific configuration of the tissue contacting surfaces of the aforementioned jaw members 14, 15, 114, 214 and 215 may be altered or modified to achieve a specific tissue effect.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
   a housing having an elongated shaft extending therefrom, the shaft defining a longitudinal axis therethrough and having a pair of first and second jaw members disposed at a distal end thereof, the first jaw member movable between an open configuration and a clamping configuration, and the second jaw member translatable along the longitudinal axis of the shaft from a retracted configuration to an extended configuration; and
   a cutting blade extending from the distal end of the shaft and operably coupled to the housing and adjacent the first and second jaw members,
   wherein the second jaw member is moveable to the extended configuration to cover a bottom portion of the cutting blade, and
   wherein the second jaw member is made from a material having relatively high thermal conductivity to facilitate cooling of the cutting blade when in the extended configuration, and wherein a bottom portion of the second jaw member is covered with a thermally insulative material to reduce thermal spread from the second jaw member to tissue adjacent the tissue of interest when the second jaw member is in the extended configuration cooling the cutting blade.

2. The ultrasonic surgical instrument according to claim 1, wherein a switching mechanism is disposed on the ultrasonic surgical instrument and is configured to actuate the second jaw member and move the second jaw member from the retracted configuration to the extended configuration.

3. The ultrasonic surgical instrument according to claim 1, wherein the second jaw member includes at least one temperature sensor thereon configured to detect a temperature of the cutting blade.

4. The ultrasonic surgical instrument according to claim 3, wherein the at least one temperature sensor is selected from the group consisting of a thermocouple and a thermistor.

5. The ultrasonic surgical instrument according to claim 1, wherein a lever is operably coupled to the housing and is configured to move the first jaw member between the open configuration and clamping configuration.

6. The ultrasonic surgical instrument according to claim 1, wherein the cutting blade is coupled to a probe that extends within the shaft.

\* \* \* \* \*